(12) United States Patent
Sutoris et al.

(10) Patent No.: US 6,475,348 B1
(45) Date of Patent: Nov. 5, 2002

(54) MIXTURE OF SUBSTANCES CONTAINING COMPOUNDS WITH VINYL GROUPS AND STABILIZERS

(75) Inventors: Heinz Friedrich Sutoris, Frankenthal; Konrad Mitulla; Jacques Dupuis, both of Ludwigshafen; Claus Kaliba, Neuhofen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/446,192

(22) PCT Filed: Jun. 4, 1998

(86) PCT No.: PCT/EP98/03338

§ 371 (c)(1),
(2), (4) Date: Dec. 17, 1999

(87) PCT Pub. No.: WO98/58038

PCT Pub. Date: Dec. 23, 1998

(30) Foreign Application Priority Data

Jun. 17, 1997 (DE) .......................................... 197 25 519

(51) Int. Cl.⁷ .............................. B01D 3/34; C07C 7/20; C09K 15/30
(52) U.S. Cl. ...................... 203/9; 203/6; 203/8; 203/57; 585/4; 585/5; 585/860; 585/864; 585/865; 252/397
(58) Field of Search .............................. 203/8, 6, 9, 57, 203/100; 252/397; 585/1, 2, 3, 4, 5, 860, 864, 865, 855

(56) References Cited

U.S. PATENT DOCUMENTS

| 3,733,326 | A |   | 5/1973 | Murayama et al. | |
|---|---|---|---|---|---|
| 5,254,760 | A | * | 10/1993 | Winter et al. ................. | 585/5 |
| 5,728,872 | A | * | 3/1998 | Riemenschneider ........ | 562/598 |
| 5,888,356 | A | * | 3/1999 | Keil et al. ...................... | 203/8 |
| 5,907,071 | A | * | 5/1999 | Arhancet ....................... | 585/5 |
| 6,218,536 | B1 | * | 4/2001 | Cunkle et al. | |

FOREIGN PATENT DOCUMENTS

| DE | 195 10 184 | | 9/1996 |
|---|---|---|---|
| DE | 196 09 312 | | 9/1997 |
| DE | 196 38 868 | | 3/1998 |
| DE | 196 51 307 | | 6/1998 |
| DE | 19926758 | * | 12/2000 |
| EP | 0 301 879 | | 2/1989 |
| EP | 0 467 848 | | 1/1992 |
| JP | 1-165534 | | 6/1989 |
| SU | 1027150 | | 10/1981 |
| SU | 1139722 | | 4/1983 |
| SU | 1558888 | | 12/1987 |
| WO | WO 96 16921 | | 6/1996 |
| WO | WO 97 46504 | | 12/1997 |
| WO | 200036052 | * | 6/2000 |

* cited by examiner

Primary Examiner—Virginia Manoharan
(74) Attorney, Agent, or Firm—Oblon, Spivak, McClelland, Maier & Neustadt, P.C.

(57) ABSTRACT

A mixture contains one or more vinyl-containing compounds as component (A) and, as a further component, a stabilizer (B) which contains one or more readily volatile nitroxyl compounds as component ($b_1$), one or more sparingly volatile nitroxyl compounds as component ($b_2$), if required one or more aromatic nitro compounds as component ($b_3$) and, if required, one or more iron compounds as component ($b_4$).

Stabilizers (B) contain the components ($b_1$) and ($b_2$), ($b_1$) and ($b_2$) and ($b_3$), ($b_1$) and ($b_2$) and ($b_4$), and ($b_1$), ($b_2$), ($b_3$) and ($b_4$), and the premature polymerization of vinyl-containing compounds during their purification or distillation is inhibited by a process in which a stabilizer (B) is added or the components of stabilizer (B) are added as individual substances or in at least two groups of the components.

12 Claims, No Drawings

MIXTURE OF SUBSTANCES CONTAINING COMPOUNDS WITH VINYL GROUPS AND STABILIZERS

The present invention relates to a mixture which contains one or more vinyl-containing compounds as a component (A) and, as a further component, a stabilizer (B) which contains one or more readily volatile nitroxyl compounds of secondary amines as component ($b_1$), one or more sparingly volatile nitroxyl compounds of secondary amines as component ($b_2$), if required as one or more aromatic nitro compounds as component ($b_3$) and, if required, one or more iron compounds as component ($b_4$).

The present invention furthermore relates to stabilizers (B), which contain the components ($b_1$) and ($b_2$), ($b_1$) and ($b_2$) and ($b_3$), ($b_1$) and ($b_2$) and ($b_4$), and ($b_1$), ($b_2$), ($b_3$) and ($b_4$), and a process for inhibiting the premature polymerization of vinyl-containing compounds during their purification or distillation by adding a stabilizer (B) or by adding the components of stabilizer (B) as individual substances or in at least two groups of the components.

It is known that many unsaturated compounds tend to undergo polymerization, as a rule free radical polymerization, while the temperature is increased. For example, vinylaromatic compounds, such as styrene or α-methylstyrene, must be stabilized with suitable compounds in order to prevent premature polymerization during the distillative purification of the crude products obtained on a large industrial scale. Usually, these stabilizers or polymerization inhibitors are added, before or during the purification step, to the crude products to be distilled. In spite of this measure, considerable proportions of polymers are still obtained. In specific cases, particularly in the event of operating faults, complete polymerization of the monomers or monomer mixtures present may take place during the purification or distillation. This results in high costs owing to the very expensive purification and the stoppage of production.

USSR patents 1,027,150, 1,558,888 and 1,139,722 describe the stabilization of styrene by using nitroxyl or bisnitroxyl compounds.

In the prior German patent application 19 510 184.7, 4-acylaminopiperidine-N-oxyl derivatives are used for stabilizing monomers capable of free radical polymerization.

The prior German patent application DE 19 609 312.0 describes compositions which contain vinyl-containing monomers and at least one N-oxyl compound of a secondary amine, the latter having no hydrogen atoms on the N-bonded carbon atoms.

Mixtures of vinylaromatic compounds with sterically hindered nitroxyl compounds, which are activated by traces of oxygen, are described in WO 96/16921.

Japanese publication Hei 1-165 534 discloses I-piperidyloxy derivatives as polymerization inhibitors for styrene. U.S. Pat. No. 3,733,326 describes the inhibition of the polymerization of vinylmonomers by using free radical precursor compounds.

Mixtures of nitroxyl and nitro compounds are described in U.S. Pat. No. 5,254,760 and prior German patent application 19 622 498.5 for stabilizing vinylaromatic compounds or vinyl-containing monomers during the purification or distillation.

Mixtures which, in addition to vinyl-containing compounds, also contain nitroxyl compounds and iron compounds and, if required, nitro compounds and costabilizers are described in prior German patent application 19 651 307.3.

The effectiveness of the stabilizers described in these publications and the stability of the additive-containing monomer mixtures are good, the higher proportion of nitro compounds described in the prior German patent application 19 622 498.5 also achieving a better retardation/effect and the presence of iron compounds in the stabilizers described in the prior German application 19 651 307.3 having a clearly favorable effect on their effectiveness. If the supply of monomers and added stabilizers to the column is stopped, these stabilizers therefore achieve a better retarding effect until the onset of extensive polymerization reactions.

In the case of all stabilizers, attention has been focused to date mainly on the stabilization of the bottom part of the column, but stabilization of monomers present in the vapor phase has been neglected. Conventional procedures in this connection are spraying in the stabilizer, also used in the bottom, in a carrier solution, for example the monomer mixture to be distilled, and/or the wetting of the column walls with, for example, the same carrier solutions to which stabilizer has been added. An even distribution of the stabilizer in the vapor phase and hence the effective stabilization thereof during the distillation/purification is not adequately ensured by such measures.

However, since in these large-scale industrial processes even small portions of polymers accumulate to give large amounts of undesirable byproducts, there is a continuous need for even more effective polymerization inhibitors. Reduction in the proportion of nitro compounds is also desirable with a view to improving the handling by the operator and reducing possible environmental pollution.

It is an object of the present invention to provide mixtures of vinyl-containing compounds which, both in the liquid and in the vapor phase, are even more effectively stabilized against premature polymerization during the purification or distillation step.

We have found that this object is achieved in an advantageous manner by mixtures which contain (A) one or more vinyl-containing compounds,
(B) a stabilizer containing
   ($b_1$) a nitroxyl compound of a secondary amine which carries no hydrogen atoms on the a carbon atoms, whose vapor pressure at the boiling point of the lowest-boiling vinyl-containing compound from (A) is from 0.01 to 50% of the vapor pressure of the lowest-boiling vinyl-containing compounds (A), or
   a mixture of nitroxyl compounds of secondary amines which carry no hydrogen atoms on the a carbon atoms, in which the vapor pressure of the highest-boiling nitroxyl compound at the boiling point of the lowest-boiling vinyl-containing compound from (A) is from 0.01 to 50% of the vapor pressure of the lowest-boiling vinyl-containing compound from (A),
   ($b_2$) a nitroxyl compound of a secondary amine which carries no hydrogen atoms on the α carbon atoms, whose vapor pressure at the boiling point of the highest-boiling vinyl-containing compound (A) is less than 0.01% of the vapor pressure of the highest-boiling vinyl-containing compound from (A), or
   a mixture of nitroxyl compounds of secondary amines which carry no hydrogen atoms on the a carbon atoms, in which the vapor pressure of the lowest-boiling nitroxyl compound at the boiling point of the highest-boiling vinyl-containing compound from (A) is less than 0.01% of the vapor pressure of the highest-boiling vinyl-containing compound from (A), in ($b_1$) and ($b_2$) the vapor pressure of the relevant pure nitroxyl compound and the vapor pressure of the relevant pure vinylaromatic compound at the boiling point of this relevant pure vinylaromatic compound being taken as the reference, ($b_3$) if required, one or more aromatic nitro compounds and, ($b_4$) if required, one or more iron compounds.

To simplify the terminology, below the component ($b_1$) and component ($b_2$) are also referred to as readily volatile and sparingly volatile component, respectively, and the nitroxyl compound present is referred to as readily volatile nitroxyl compound (or a mixture of readily volatile nitroxyl compounds) or as sparingly volatile nitroxyl compound (or a mixture of sparingly volatile nitroxyl compounds).

A preferred mixture is one which contains, as component (A), vinyl-containing compounds of the formula Ia

where $R^1$ is hydrogen, $C_1$–$C_4$-alkyl, $C_2$–$C_4$-alkenyl, carboxyl, formyl, sulfo, hydroxyl, amino or nitro $R^2$ is $C_2$–$C_4$-alkenyl and/or vinyl-containing compounds of the formula Ib

where $R^3$ is hydrogen or $C_1$–$C_4$-alkyl and $R^4$ is $C_2$–$C_4$-alkenyl.

The $C_1$–$C_4$-alkyl groups $R^1$ and $R^3$ may be methyl, ethyl, propyl, 2-propyl, 1-butyl, 2-butyl, 2-methyl-1-propyl or tert-butyl. Suitable $C_2$–$C_4$-alkenyl groups $R^1$, $R^3$ and $R^4$ are vinyl, 1-propenyl, 1-butenyl, 1-methyl-1-ethenyl, 1-methyl-1-propenyl, 2-methyl-1-propenyl (isobutenyl) and 1-ethyl-1-ethenyl. Examples of compounds of the formula Ia are styrene, α-methylstyrene, p-, m-, and o-nitrostyrene, p-, m- and o-styrenesulfonic acid, p-, m-and o-vinyltoluene, p-, m- and o-divinylbenzene, p-, m- and o-vinylaniline and p-, m- and o-vinylphenol, in the case of the isomeric vinylaromatic compounds, the o-isomer being obtained in practice only in small amounts—if at all—in the conventional large-scale industrial production.

Examples of compounds of the formula Ib are:

2-, 3- and 4-vinylpyridine and the various isomers of the methylvinylpyridine, for example the industrially important 2-methyl-5-vinylpyridine. Among the vinylpyridine isomers, 2-and 4-vinylpyridine are particularly noteworthy as important large-scale industrial products.

of course, mixtures of compounds of the formula Ia or of the formula Ib or mixtures of compounds of the formulae Ia and Ib may be present in the novel mixture.

A further preferred mixture contains, as component (A), vinyl-containing compounds of the formula II $$CH_2=CZ^4—Q—Z^1 \qquad (II)$$

where

Q is a chemical single bond, oxygen or —$NZ^2$—, $Z^1$ is

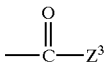

or—$Z^3$, $Z^2$, $Z^4$ are each hydrogen or $C_1$–$C_4$-alkyl and, $Z^3$ is hydrogen, hydroxyl, cyano, $C_1$–$C_8$-alkoxy, $C_1$–$C_8$-alkyl or a radical which, together with $Z^2$ or $Z^4$, forms a saturated or unsaturated $C_3$-, $C_4$-, $C_5$- or $C_6$-alkylene bridge, in which up to two non-neighboring carbon atoms may be replaced by N, NH, N($C_1$–$C_4$-alkyl), N($C_6$–$C_{10}$-aryl) or oxygen.

If, in the formula II Q is a chemical single bond, $Z^1$ is either —CO—$Z^3$ or $Z^3$ alone. Particularly suitable radicals $Z^3$ here are hydroxyl and $C_1$–$C_8$-alkoxy, such as methoxy, ethoxy, propoxy, tert-butoxy, n-butoxy or 2-ethylhexyloxy, in the first case and cyano in the latter case.

$Z^4$ is hydrogen or $C_1$–$C_4$-alkyl, hydrogen and methyl being preferred radicals. Preferred compounds (A) of the formula II in the novel mixture are therefore acrylic acid, methacrylic acid, the corresponding methyl, ethyl, propyl, tert-butyl, n-butyl and 2-ethylhexyl esters and acrylonitrile and methacrylonitrile.

In the compounds (A) of the formula II which are present in the novel mixture, Q may furthermore be oxygen. Preferred among these compounds are the vinyl esters, in which $Z^1$ is —CO—$Z^3$ and the vinyl ethers, in which $Z^1$ is identical to $Z^3$ and in which $Z^3$ is preferably $C_1$–$C_8$-alkyl, eg. methyl, ethyl, n-propyl, isopropyl, n-butyl, isobutyl, sec-butyl, tert-butyl or 2-ethylhexyl.

If Q is —$NZ^2$—, $Z^1$ is preferably —CO—$Z^3$.

Suitable radicals $Z^3$ in addition to the abovementioned ones are also those radicals which, for example together with —$NZ^2$—, form a saturated or unsaturated 5- to 7-membered ring. Examples of such ring systems are:

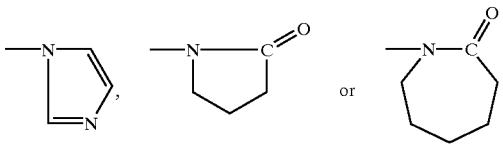

in particular the N-pyrrolidinonyl and the N-caprolactamyl radical.

The $C_6$–$C_{10}$-aryl radicals mentioned for the radicals N($C_6$–$C_{10}$-aryl) of the group $Z^3$ preferably comprise phenyl which may be substituted by one or more $C_1$–$C_4$-alkyl radicals. Where two or more substituents are present, the sum of their carbon atoms should not exceed four. Examples of substitution patterns on the benzene ring are three methyl groups, one methyl and one propyl group or only one tert-butyl group. Further examples of $C_1$–$C_4$-alkyl radicals which may also be present in the radicals N($C_1$–$C_4$-alkyl) of the group $Z^3$ have been stated above. Furthermore, the suitable $C_{10}$-aryl radical is naphthyl.

Further preferred compounds (A) in the novel mixture are N-vinylformamide, N-vinyl-2-pyrrolidone and N-vinyl-ε-caprolactam.

The choice of suitable nitroxyl compounds as components ($b_1$) and ($b_2$) of the stabilizer (B) is advantageously based on the vinyl-containing compounds of component (A), which—as pure substance—have the lowest and highest boiling point, respectively (in each case at the same reference pressure p). These compounds identified in this manner are denoted by $\alpha_1$ and $\alpha_2$, respectively, and their boiling points by $T_1(p)$ and $T_2(p)$. Since boiling points are frequently available for atmospheric pressure (1013 hPa), for the readily volatile and sparingly volatile vinyl-containing compounds $\alpha_1$ and $\alpha_2$ respectively, $$p(\alpha_1)=p(\alpha_2)=p=1013 \text{ hPa}$$

and $$T_1(p)<T_2(p),$$

corresponding to the terms low-boiling and high-boiling, respectively. For a readily volatile nitroxyl compound as component ($b_1$), referred to here as $\beta_1$, it is therefore generally true, according to the invention, that $$0.0001 \cdot p(\alpha_1, T_1) \leq p(\beta_1, T_1) \leq 0.50 \cdot p(\alpha_1, T_1) \qquad (1)$$

and, for a sparingly volatile nitroxyl compound as component ($b_2$), referred to here as $\beta_2$, according to the invention the following general expression may be written $$p(\beta_2, T_2)<0.0001 \cdot p(\alpha_2, T_2) \qquad (2),$$

where $p(\alpha_1, T_1)$, $p(\alpha_2, T_2)$, $p(\beta_1, T_1)$ and $p(\beta_2, T_2)$ are the vapor pressures of the pure compounds $\alpha_1$, $\alpha_2$, $\beta_1$ and $\beta_2$, respectively, at the corresponding temperatures $T_1$, $T_2$. If these vapor pressures correspond to atmospheric pressure ("reference pressure") of 1013 hPa, the relationships (1) and (2) can be rewritten as $$0.0001 \cdot 1013 \text{ hPa} \leq p(\beta_1, T_1) \leq 0.50 \cdot 1013 \text{ hPa} \qquad (1')$$

and $$p(\beta_2, T_2)<0.0001 \cdot 1013 \text{ hPa} \qquad (2').$$

If a plurality of readily volatile nitroxyl compounds ($\beta_1^1, \beta_1^2, \beta_1^3 \ldots$) are to be used as component ($b_1$) and a plurality of sparingly volatile nitroxyl compounds ($\beta_1^1, \beta_1^2, \beta_1^3 \ldots$) as component ($b_2$) of the stabilizer (B), these compounds must, according to the invention, each individually and as pure substances, satisfy the relationships (1) and (2), ie.

$$0.0001 \cdot p(\alpha_1, T_1) \leq p(\beta_1^1, T_1) \leq 0.50 \cdot p(\alpha_1, T_1),$$

$$0.0001 \cdot p(\alpha_1, T_1) \leq p(\beta_1^2, T_1) \leq 0.50 \cdot p(\alpha_1, T_1),$$

$$0.0001 \cdot p(\alpha_1, T_1) \leq p(\beta_1^3, T_1) \leq 0.50 \cdot p(\alpha_1, T_1),$$

.

.

.

and $$p(\beta_2^1, T_2)<0.0001 \cdot p(\alpha_2, T_2),$$

$$p(\beta_2^2, T_2)<0.0001 \cdot p(\alpha_2, T_2),$$

$$p(\beta_2^3, T_2)<0.0001 \cdot p(\alpha_2, T_2),$$

.

.

.

where of course relationships corresponding to (1') and (2') can be set up for the case where $p(\alpha_1, T_1)=p(\alpha_2, T_2)=1013$ hPa.

In distillations, for example, isothermal conditions are present (ideally), so that the following expressions may be written for the lowest- and highest-boiling vinyl-containing compounds $\alpha_1$ and $\alpha_2$, respectively $$p(\alpha_1, T_1)=p(\alpha_1, T)$$

and $$p(\alpha_2, T_2)=p(\alpha_2, T),$$

where furthermore $$p(\alpha_1, T)=p(\alpha_1)<p(\alpha_2, T)=p(\alpha_2)$$

where $T_1=T_2=T$.

For the (vapor-phase) temperature T ($=T_1=T_2$) considered, the following are accordingly obtained, according to the invention, with respect to the relationships (1) and (2)

$$0.0001 \cdot p(\alpha_1) \leq p(\beta_1, T)=p(\beta_1) \leq 0.50 \cdot p(\alpha_1)$$

and $$p(\beta_1, T)<0.0001 \cdot p(\alpha_2),$$

where $p(\alpha_1)$, $p(\alpha_2)$, $p(\beta_1)$ and $p(\beta_2)$ are the vapor pressures of the relevant pure substances $\alpha_1$, $\alpha_2$, $\beta_1$ and $\beta_2$ at the temperature T considered.

The choice of suitable nitroxyl compounds as components ($b_1$) and ($b_2$) is based on their vapor pressure curves, as well as the corresponding data for the vinyl-containing compounds (A), which are to be stabilized both in the liquid and in the vapor phase. The vapor pressure curves of the latter compounds are in most cases readily available from the relevant literature, but the data for the former compounds are generally not available. However, vapor pressures as a function of temperature can be determined readily and routinely for most substances, so that these data can generally be quickly obtained by a person skilled in the art. They form the working basis in plants involved in the distillation/purification of vinyl-containing compounds.

If basic data, such as the heat of vaporization and the boiling point at the associated pressure, are available for a compound, it is also possible to extrapolate approximately to other pressure/temperature pairs with the aid of the Clausius-Clapeyron equation.

Nitroxyl compounds which can be used either in the readily volatile component ($b_1$) or in the sparingly volatile component ($b_2$) are described, for example, in the prior German application 196 51 307.3. Selection in accordance with the molar mass of the nitroxyl compound may serve as a rule of thumb. Usually, compounds having high molar masses, for example including the nitroxyl compounds described in the prior German application 196 51 307.3, which contain two or more 1-N-oxyl-2,2,6,6-tetramethyl-piperidine units in the molecule, are more sparingly volatile than compounds having low molar masses, for example the nitroxyl compounds described in the abovementioned prior German publication which have only one 1-N-oxyl-2,2,6,6-tetramethyl-piperidine unit or the N-oxyl compounds of the formula

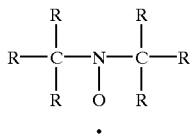

which are likewise mentioned in this publication, but, where the radicals R stated in this prior German publication are aralkyl or aryl groups and not lower alkyl groups, more sparingly volatile nitroxyl compounds must once again be expected.

However, since the volatility depends only in part on the molar mass but also to a high degree on structural aspects of the compounds considered, such as the presence of polar groups, intermolecular and intramolecular interactions, etc., the molar mass of the nitroxyl compounds considered can, as stated above, serve only as the first indication. The suitability of a compound as a constituent of component ($b_1$) or component ($b_2$) can be checked only with regard to the vinyl-containing compounds of component (A) which are to be stabilized. A good guide in this respect is generally provided simply by the easily determined boiling point of the nitroxyl compound, provided this compound has a boiling point, possibly also at reduced pressure, comparable with the boiling point or the boiling points of the vinyl-containing compound or compounds. With the aid of the Pictet-Trouton rule and the Clausius-Clapeyron equation, it is then possible to make estimates with regard to the pressure/temperature behavior deviating from the determined boiling point. The Pictet-Trouton rule (often also referred to only as the Trouton rule) states that the molar entropy of vaporization assumes the value of about 88 $J \cdot mol^{-1} \cdot K^{-1}$.

This rule is generally well complied with by non-polar substances. However, deviations occur in the case of strongly associating compounds.

According to the invention, a preferably used readily volatile component ($b_1$) comprises one or more compounds of the formula IIIa

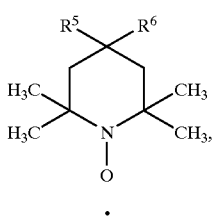

where $R^5$ is hydrogen, and $R^6$ is hydrogen, hydroxyl, $C_1$–$C_4$-alkoxy, $C_1$–$C_6$-acyloxy or tri($C_1$–$C_4$-alkyl)silyloxy or $CR^5R^6$ together is carbonyl and a preferably used sparingly volatile component ($b_2$) comprises one or more compounds of the formula IIIb

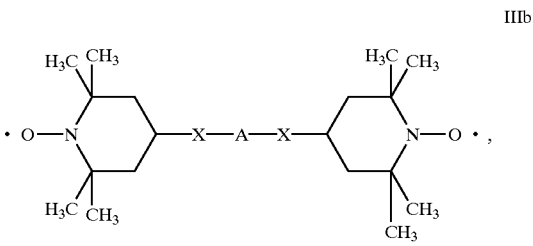

where

X is oxygen or $R^7$—N,

A is $C_6$–$C_{12}$-alkylene, α,ω-bis(carbonyloxy)-$C_6$–$C_{12}$-alkylene, α,ω-$C_6$–$C_{12}$-diacyl, 1,2-, 1,3- or 1,4-phenylene, phthaloyl, isophthaloyl or terephthaloyl, $R^7$ is hydrogen, $C_1$–$C_4$-alkyl or $C_1$–$C_6$-acyl.

Here, the $C_1$–$C_4$-alkoxy groups $R^6$ of compound IIIa comprise methoxy, ethoxy, propoxy, 2-propoxy, butoxy, 2-butoxy, 2-methylpropoxy (isobutoxy) and tert-butoxy. The $C_1$–$C_6$-acyloxy groups $R^6$ are to be understood as meaning formate, acetate, propionate, butanoate, pentanoate (valerate), hexanoate (capronate) and the isomeric groups, for example 2-methylpropionate (isobutanoate), 3-methylbutanoate (isovalerate), 2-methylbutanoate, neopentanoate or 2-, 3- or 4-methylpentanoate (2-, 3- or 4-methylvalerate). The silyloxy groups trisubstituted by identical $C_1$–$C_4$-alkyl groups are preferably used in the case of the tri($C_1$–$C_4$-alkyl)silyloxy groups $R^6$. Suitable $C_1$–$C_4$-alkyl groups are the alkyl radicals contained in the above-mentioned $C_1$–$C_4$-alkoxy groups. Suitable silyloxy groups are therefore, for example

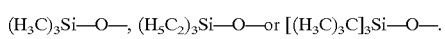

In specific cases, however, it is also possible to use silyloxy radicals having a mixture of substituents, for example

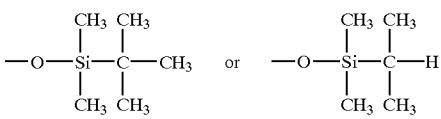

Examples of readily volatile nitroxyl compounds as a constituent of component ($b_1$) are

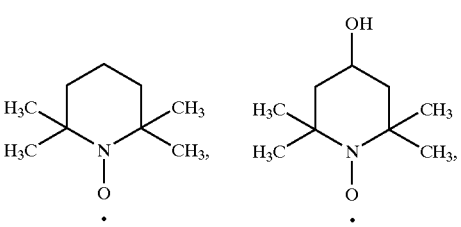

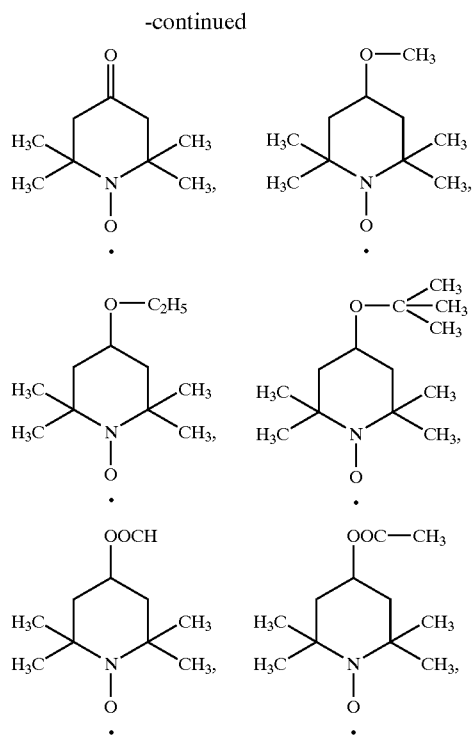
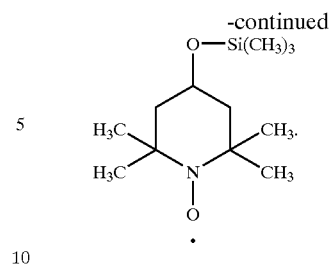

Examples of possible $C_{1-C_4}$-alkyl groups $R^7$ in the compounds of the formula IIIb have already been discussed under radical $R^6$ of compounds of the formula IIIa. Accordingly, the groups contained in the abovementioned acyloxy groups $R^6$ can be used as $C_1$–$C_6$-acyl groups $R^7$. In the case of the $C_6$–$C_{12}$-alkylene, α,ω-bis(carbonyloxy)-$C_6$–$C_{12}$-alkylene and α,ω- —$C_6$–$C_{12}$-diacyl groups stated under the bridging group A, the linear groups —$(CH_2)_l$—, —OOC—$(CH2)_m$—COO— and —(CO)O—$(CH_2)_n$—O(CO)— (where 1, m and n are integers from 6 to 12, 4 to 10 and 6 to 12, respectively) are preferably used. However, branched bridges A are also possible.

Examples of sparingly volatile nitroxyl compounds which can be used as a constituent of component ($b_2$) are

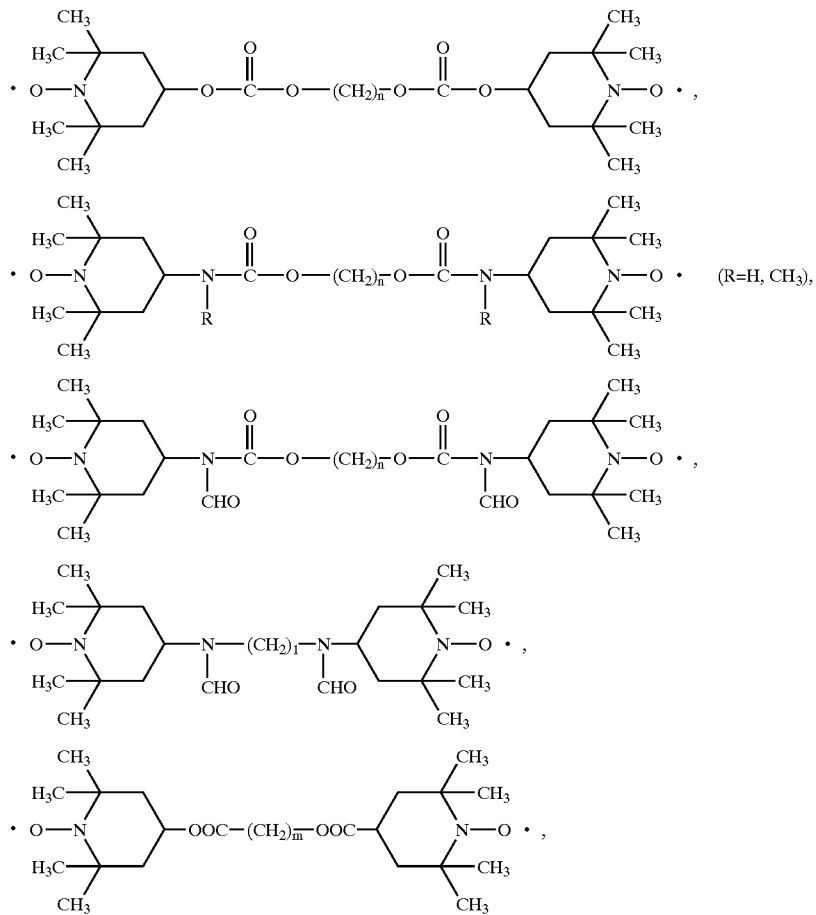

-continued

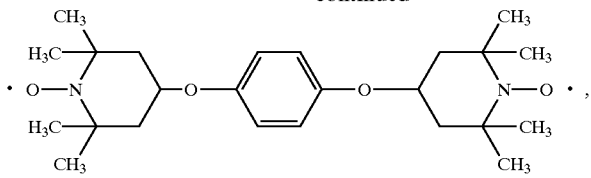

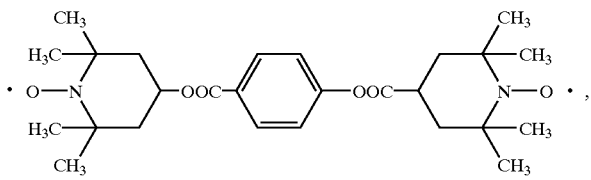

The indices 1, m and n may assume the abovementioned numerical values.

In particular, the compounds
bis(1-N-oxyl-2,2,6,6-tetramethylpiperidin-4-yl) adipate,
bis(1-N-oxyl-2,2,6,6-tetramethylpiperidin-4-yl) sebacate,
N,N'-bis(1-N-oxyl-2,2,6,6-tetramethylpiperidin-4-yl) adipamide,
N,N'-bis(1-N-oxyl-2,2,6, 6-tetramethylpiperidin-4-yl) sebacinamide,
N,N'-bis(1-N-oxyl-2,2,6,6-tetramethylpiperidin-4-yl)-N,N'-bisformyl-1,6-diaminohexane are used.

The compounds of the formulae IIIa and IIIb can be easily prepared, or some of them are commercially available, for example the compound

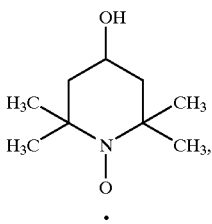

("Tempo1")

which can be obtained from Hüls and can be used for the preparation of the corresponding dimer compounds of the formula IIIb.

On the other hand, it is also possible first to prepare the piperidine derivatives on which the compound as IIIa and IIIb are based and to convert them in a final oxidation step, for example by means of hydrogen peroxide, into the corresponding nitroxyl compounds. Examples of such preparations are to be found in the prior German application 196 51 307.3 and the literature cited therein.

The stated readily volatile and sparingly volatile compounds IIIa and IIIb, respectively, are preferably used in a mixture which contains the abovementioned vinyl-containing compounds of the formulae Ia and/or Ib and of the formula II as component (A). However, the compounds of the formulae IIIa and IIIb can also be used for any other vinyl-containing compounds whose boiling points and vapor pressures meet the criteria according to the invention with respect to the data of the nitroxyl compounds.

In addition to component (A) and stabilizer (B), the novel mixture can, if required, also contain one or more aromatic nitro compounds and, if required, also one or more iron compounds.

Suitable nitro compounds are described, for example, in the prior German patent application 196 51 307.3. In particular, these are compounds such as 1,3-dinitrobenzene 1,4-dinitrobenzene, 2,6-dinitro-4-methylphenol, 2-nitro-4-methylphenol, 2,4, 6-trinitrophenol, 2,4-dinitro-1-naphthol, 2,4-dinitro-6-methylphenol, 2,4-dinitrochlorobenzene, 2,4-dinitrophenol, 2,4-dinitro-6-sec-butylphenol, 4-cyano-2-nitrophenol and 3-iodo-4-cyano-5-nitrophenol. Aromatic nitro compounds, such as 2,6-dinitro-4-methylphenol, 2-nitro-4-methylphenol, 2,4-dinitro-6-sec-butylphenol and 2,4-dinitro-6-methylphenol are preferably used.

Iron compounds are likewise mentioned in the prior German patent application 196 51 307.3. These are in particular iron compounds from the groups consisting of the a) iron carbonyls and carbonyl ferrates, b) organometallic iron carbonyl compounds, c) unsubstituted and substituted ferrocene compounds, d) iron compounds having ligands which contain oxygen, nitrogen, sulfur or phosphorus as donor atoms alone or mixed and, e) iron halide and iron pseudohalide compounds.

Iron compounds from the groups a) and b), are preferably used, particularly preferably from the group d). In the latter group, particularly suitable iron complexes are those with heteroannulenes (eg. azoannulene), eg. iron dibenzo[b,i]-1, 4,8,11-tetraaza-(14)annulene (Fe(taa)), or the iron complexes with (substituted and/or benzofused) phthalocyanines. The formulae of the compounds are shown below:

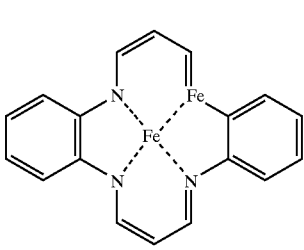

(Fe(taa))

and

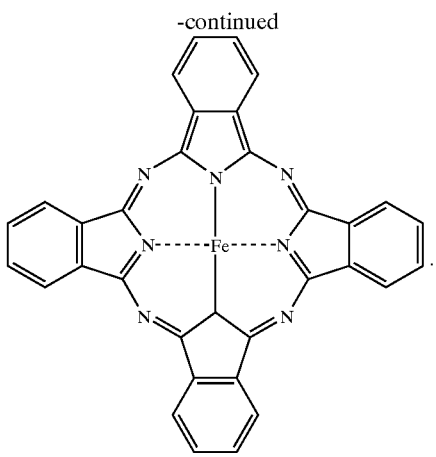

In addition, the novel mixture can, if desired, also contain, for example, one or more costabilizers from the group consisting of the aromatic nitroso compounds, phenothiazines, quinones, hydroquinones and ethers thereof, phenols and ethers thereof, hydroxylamines and phenylenediamines.

Examples of suitable aromatic nitroso compounds are p-nitrosophenol, p-nitroso-o-kresol and p-nitroso-N,N'-diethylaniline.

Further costabilizers can also be substituted phenols or hydroquinones, for example the following:
4-tert-butylpyrocatechol, methoxyhydroquinone,
2,6-di-tert-butyl-4-methylphenol,
n-octadecyl-β-(3,5-di-tert-butyl-4-hydroxyphenyl) propionate,
1,1,3-tris-(2-methyl-4-hydroxy-5-tert-butylphenyl)butane,
1,3,5-trimethyl-2,4,6-tris-(3,5-di-tert-butyl-4-hydroxybenzyl)-benzene, 1,3,5-tris-(3,5-di-tert-butyl-4-hydroxybenzyl) isocyanurate, 1,3,5-tris-[β-(3,5-di-tert-butyl-4-hydroxyphenyl) propionyloxyethyl] isocyanurate,
1,3,5-tris-(2,6-dimethyl-3-hydroxy-4-tert-butylbenzyl) isocyanurate or pentaerythrityl tetrakis-[β-(3,5-di-tert-butyl-4-hydroxyphenyl)-propionate].

According to the invention, a stabilizer (b) which contains in each case one or more nitroxyl compounds of the formulae IIIa and IIIb as components ($b_1$) and ($b_2$) is claimed.

Another stabilizer (B) claimed according to the invention is one which, in addition to the compounds of the formulae IIIa and IIIb (as components ($b_1$) and ($b_2$)), also contains one or more aromatic nitro compounds as component ($b_3$).

According to the invention, a stabilizer which contains one or more iron compounds as component ($b_4$) in addition to the nitroxyl compounds of the formulae IIIa and IIIb is furthermore claimed.

According to the invention, a stabilizer which contains one or more aromatic nitro compounds and one or more iron compounds as components ($b_3$) and ($b_4$) in addition to the nitroxyl compounds of the formulae IIIa and IIIb is furthermore claimed. Examples of the nitroxyl compounds, aromatic nitro compounds and iron compounds have been mentioned further above.

If desired, further additives, eg. the costabilizers likewise discussed above, can of course also be added to the stated novel stabilizers (B).

The stated stabilizers (B) contain the components ($b_1$) and ($b_2$) in an amount of from 1 to 99% by weight and from 99 to 1% by weight, respectively, based on the total amount of components ($b_1$) and ($b_2$). If the component ($b_1$) contains one or more nitroxyl compounds of the formula IIIa which are to be regarded as very volatile with respect to the vinyl-containing compound (or compounds), for example subjected to distillation, ie. if, in accordance with the criterion described at the outset, they have vapor pressures of a few percent or a few ten percents of the vapor pressure of the lowest-boiling vinyl-containing compound of component (A) at the boiling point of said vinyl-containing compound, the amount of component ($b_1$) can be brought to below 99% by weight and accordingly the amount of component ($b_2$) to above 1% by weight.

If on the other hand, in the abovementioned sense, component ($b_1$) is to contain nitroxyl compounds of relatively low volatility, its proportion of the total mixture of components ($b_1$) and ($b_2$) is preferably brought to a higher level.

With the addition of aromatic nitro compounds, as component ($b_3$) to the stabilizer (B), the ratio of the amount of component ($b_3$) to the amount of the nitroxyl compounds (the sum of the amounts of components ($b_1$) and ($b_2$)) can be varied as desired. Since nitroxyl compounds are generally relatively expensive, however, it will be wished to keep their proportion of the stabilizer as small as possible.

Usually, such mixtures then comprise from 0.05 to 4.5% by weight of nitroxyl compounds (sum of components ($b_1$) and ($b_2$)) and from 95.5 to 99.95% by weight of aromatic nitro compounds, the proportions being based on the total amount of the components ($b_1$), ($b_2$) and ($b_3$).

If, in addition to the components ($b_1$) and ($b_2$), iron compounds, as component ($b_4$), are added to the stabilizer (B), their proportion is usually from 1 ppm to 5% by weight, preferably from 10 ppm to 3% by weight, based on the total amount of the components ($b_1$), ($b_2$) and ($b_4$).

If, in addition to the nitroxyl compounds, both components ($b_3$) and component ($b_4$) are also present, their proportions are calculated similarly to the above stabilizers (B), which contain the nitroxyl compounds (as components ($b_1$) and ($b_2$)) and aromatic nitro compounds (as component ($b_3$)) or iron compounds (as component ($b_4$)). For a stabilizer (B), which contains the components ($b_1$), ($b_2$), ($b_3$) and ($b_4$), the proportion of component ($b_3$), based on the sum of the components ($b_1$), ($b_2$) and ($b_3$) may thus be adjusted as desired. Usually, the proportion of ($b_3$), based on the sum of ($b_1$), ($b_2$) and ($b_3$), is from 95.5 to 99.95% by weight. The proportion of component ($b_4$), based on the sum of components ($b_1$), ($b_2$) and ($b_4$), is usually from 1 ppm to 5% by weight, preferably from 10 ppm to 3% by weight.

If, for example, costabilizers as stated above are also added to the stabilizers (B), their proportion, based on the total amount of the components ($b_1$), ($b_2$), if required ($b_3$) and/or if required ($b_4$) and the costabilizer (the costabilizers) is from 0.01 to 20% by weight.

The stabilizer (B) is present in the novel mixture usually in a proportion of from 0.0002 to 5, preferably from 0.0005 to 0.5, % by weight, based on the total amount of the mixture of component (A) and stabilizer (B).

Under inert conditions, eg. under a nitrogen atmosphere, it is advantageous to use stabilizers (B) with at least one nitro compound as component ($b_3$) and, if required, an iron compound as component ($b_4$). The suitable ratio of nitroxyl compounds to component ($b_3$) is dependent on the individual boundary conditions, for example the chemical nature of the compounds (A) to be stabilized, the temperature ranges to maintain, for example, during a distillation (important, inter alia, with respect to the volatility and hence the distribution of the components ($b_1$) and ($b_3$) between vapor and liquid phase), or the (residual) oxygen content in the unit used. However, it is possible for a person skilled in the art to determine an optimized ratio of these components by means of preliminary experiments, taking into account the particular circumstances. Usually, however, stabilizers (B) having a content, discussed above, of from 95.5 to 99.95% by weight of the aromatic nitro compounds should exhibit good efficiency.

If the compounds (A) to be stabilized are exposed to an atmosphere which also contains (residual) oxygen, the proportion of nitro compounds can be reduced or their use can be dispensed with entirely. This is desirable particularly with respect to safety in the handling of such inhibitors as well as from the point of view of reducing possible harmful effects on the environment. Thus, nitroxyl compounds alone (ie. stabilizers (B) which contain only components ($b_1$) and ($b_2$)), but to an even greater extent iron-containing stabilizers (B) without the addition of nitro compounds, stabilize component (A) very well to undesired premature polymerization at oxygen contents of from about 0.5 ppm to a few 10 000 ppm, as can be found, inter alia, in conventional large-scale industrial distillation columns.

Stabilizer (B)—if desired as a mixture with nitro compounds ($b_3$) and/or iron compounds ($b_4$) and/or if desired costabilizers—can be added to the vinyl-containing compounds (A) before or during the purification or distillation, as such, as a suspension or as a solution, with the use of a suitable solvent or solvent mixture, in an effective amount in order to suppress premature polymerization. In a specific case, it may also be necessary to add the components ($b_1$) and ($b_2$) of the stabilizer (B) and, if required, nitro compounds ($b_3$) and/or iron compounds ($b_4$) and/or one or more of the stated costabilizers separately and, in this case, preferably at spatially separate points.

Furthermore, it may be necessary to add part-mixtures, ie. groups of components, for example a mixture of component ($b_2$) with nitro compounds ($b_3$) and/or iron compounds ($b_4$) and/or possibly mixed with further costabilizers on the one hand and component ($b_1$) on the other hand separately, and, in this case, preferably at spatially different points.

Suspensions or solutions of the stabilizers (B) are preferably prepared with water. Alkanols, such as methanol, ethanol, propanol, n-butanol, isobutanol and tert-butanol, if required as a mixture with water, are also preferably used. These alcohols or mixtures thereof with water are preferably used in the case of the corresponding esters of acrylic acid and alkyl acrylic acid, ie. in the case of vinyl-containing compounds of the formula II.

Furthermore, ketones, such as acetone, methyl ethyl ketone, methyl propyl ketone or methyl butyl ketone, diols such as glycol or propylene glycol or propylene glycol and their alkyl mono- or diethers, oligomeric or polymeric ethylene glycols (polyethylene glycols) and propylene glycols (polypropylene glycols) and their alkyl ethers, diamines, such as ethylenediamine or propylenediamine, and their alkyl mono- or diiminoethers, oligomeric or polymeric ethylenediamines (polyethyleneimines) and their alkyl iminoethers may be used, if required as a mixture with alcohols and water, as suspending agents or solvents. The compounds (A) used or mixtures thereof may of course also be used as solvents or suspending agents.

Crude product mixtures may also be used for this purpose. If, for example, oven oil, a mixture obtained in the dehydrogenation of ethylbenzene and comprising predominantly styrene, ethylbenzene, toluene and other substituted aromatics, is to be purified by distillation, this mixture can be used as a solvent and/or suspending agent. Of course, it is also possible to use ethylbenzene or toluene as a pure substance for the solution and/or suspension.

The novel stabilizers (B) can also be used—as such or as a suspension or solution—generally for inhibiting the premature polymerization of compounds, preferably those capable of free radical polymerization, and display their stabilizing effect in a wide temperature range. They are effective at any conventional storage temperature from −50 to +50° C. The pressure range of the stabilizing process is not critical. The stabilizers are effective at atmospheric pressure or at reduced or superatmospheric pressure.

The statements below are intended to illustrate the concept of the invention without restricting the scope of the invention.

Table 1 shows various compounds of the formula IIIa, with their boiling points dependent on the equilibrium pressure (own measurements).

The stated compounds are as follows:

Tempo [SiC]:

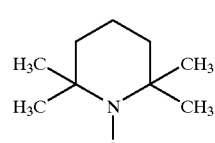

Oxo-Tempo [SiC]:

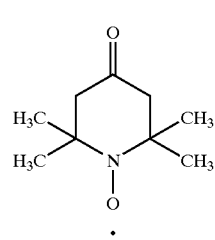

and with the respective radicals R in the formula

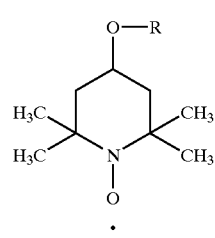

Ac-Tempol for R=acetyl, Tempol for R=H, Me-Tempol for R=methyl, Et-Tempol for R=ethyl and TMS-Tempol for R=trimethylsilyl.

TABLE 1

| Pressure (hPa) | Tempo [sic] | Ac-Tempol | Tempol | Me-Tempol | Et-Tempol | TMS-Tempol | Oxo-Tempo [Sic] |
| --- | --- | --- | --- | --- | --- | --- | --- |
| 0.5 | 22.9 | 71.2 | 89.1 | 49.1 | 56.1 | 60.9 | 60.2 |
| 1 | 32.6 | 82 | 99.56 | 59.2 | 66.2 | 71.4 | 70.2 |
| 2 | 43.2 | 93.5 | 110.84 | 70.2 | 77.2 | 82.8 | 81.1 |
| 5.3 | 59.7 | 111.1 | 128.1 | 87.3 | 94.2 | 110.4 | 98.1 |
| 6.7 | 64 | 115.6 | 132.6 | 91.7 | 98.7 | 105 | 102.5 |
| 12.5 | 76.1 | 128.1 | 145 | 104.2 | 111.2 | 117.8 | 115 |

At the pressures stated in hPa, the compounds shown in Table 1 have the boiling point corresponding to the numerical value in ° C.

Table 2 shows a selection of vinyl-containing compounds of the formulae Ia and Ib and Table 3 a selection of vinyl-containing compounds of the formula II, with their respective boiling points. In each case, the numerical values (to be understood as hPa) of the corresponding vapor pressures at the stated boiling point are shown, if these pressures differ from atmospheric pressure (1013 hpa).

Tables 2 and 3 furthermore indicate the literature references for the boiling points. Where the volume and the year are stated in addition to the page number, the data have been taken from Römpp-Chemielexikon (Georg Thieme Verlag Stuttgart-New York). If only the page number is stated, the data originate from the Chemiker-Kalender (3rd edition, Springer-Verlag Berlin, Heidelberg, New York, Tokyo, (1983)).

TABLE 2

| Compound | Boiling point in ° C. | Literature reference |
|---|---|---|
| Styrene | 145.8 | Volume 5, page 4355/6, (1992) |
| a-Methylstyrene | 165 | Volume 4, page 2761, (1991) |
| Vinyltoluene | 172 (m:p = 60:40)* | Volume 6, page 4927, (1992) |
| Divinylbenzene | 195 (m:p = 75:25)* | Volume 2, page 1018/9, (1990) |
| 2-Vinylpyridine | 49–51 (15) | Volume 6, page 4926, (1992) |
| 4-Vinylpyridine | 62–65 (20) | Volume 6, page 4926, (1992) |
| 2-Methyl-4-vinyl-pyridine | 181 | Volume 4, page 2763, (1991) |

*Proportions of m- and p-isomers in a mixture with the stated boiling point

TABLE 3

| Compound | Boiling point in ° C. | Literature reference |
|---|---|---|
| Acrylonitrile | 77.5 | page 199 |
| Acrylic acid | 141 | page 199 |
| Methyl acrylate | 80.5 | page 199 |
| Ethyl acrylate | 99–100 | page 199 |
| Butyl acrylate | 145 | page 199 |
| Methacrylic acid | 159 (989) | page 319 |
| Methyl methacrylate | 100.3 | page 319 |
| Ethyl methacrylate | 116.5 | page 319 |
| Vinylmethyl ether | 5.5 | Volume 6, page 4924, (1992) |
| Vinylethyl ether | 35.5 | Volume 6, page 4924, (1992) |
| Vinyl-n-butyl ether | 94 | Volume 6, page 4924, (1992) |
| Vinyl-isopropyl ether | 83 | Volume 6, page 4924, (1992) |
| 1-Vinyl-2-pyrrolidone | 215, 96 (19) | Volume 6, page 4926, (1992) |
| N-Vinylformamide | 84.2 (12.5) | own measurement |

If, for example, styrene is to be stabilized both in the liquid and in the vapor phase during the distillation and the latter is carried out at atmospheric pressure, according to the invention it is necessary to select a volatile nitroxyl compound ($b_1$) which has from 0.01 to 50% of the vapor pressure of styrene (1013 hPa) at the boiling point of styrene, 145.8° C., under these conditions. According to Table 1, it is immediately clear that the compound Tempol having a vapor pressure of 12.5 hPa at 145° C. (≈145.8° C.) fulfills this criterion (12.5/1013=1.2%).

The following procedure may be used for estimating whether the compound Tempo [sic] is suitable:
according to Table 1, Tempo [sic] has a vapor pressure of 12.5 hPa at 76.1° C. The vapor pressure $p(T_2)$ of the nitroxyl compound can be calculated according to the Clausius-Clapeyron equation in its approximate form $$\ln p(T_2) - \ln p(T_1) = \frac{L}{R}(1/T_1 - 1/T_2),$$

where $T_1$ and $T_2$ are different boiling points, ie. $T_1$=76.10° C. and $T_2$=145.8° C. in this case, $p(T_1)$ and $p(T_2)$ are the associated vapor pressures, ie. $p(T_1)$=12.5 hPa and $p(T_2)$ is the desired vapor pressure in this case, L is the heat of vaporization, in is the natural logarithm to the base E and R is the gas constant (8.314 J·mol$^{-1}$K$^{-1}$). The Pictet-Trouton rule permits an estimate of the heat of vaporization L at 76.1° C. and 145.8° C. as $$L(76.1° \text{ C.}) \approx 88 \text{ J·mol}^{-1}\text{K}^{-1} \cdot (273.15 + 76.1) \text{ K}$$
$$= 30734 \text{ J·mol}^{-1}$$

and $$L(145.8° \text{ C.}) \approx 88 \text{ J·mol}^{-1}\text{K}^{-1} \cdot (273.15 + 145.8) \text{ K}$$
$$= 36867.6 \text{ J·mol}^{-1}.$$

If these values are substituted for L in the approximate form of the Clausius-Clapeyron equation, a vapor pressure which is between 72.7 hPa (L(76.1° C.)) and 103.3 hPa (L(145.8° C.)) at 145.8° C. is obtained for the compound Tempo [sic]. Both values fulfilled the criterion according to the invention (72.7/1013=7.2% or 103.3/1013=10.2%).

Tempo [sic] is therefore also suitable as component ($b_1$) for stabilizing styrene to distillation at atmospheric pressure, and the remaining nitroxyl compounds shown in Table 1 are therefore also suitable. If styrene is to be distilled under reduced pressure, which is also usually the case, the pressure/temperature conditions then applicable to styrene can be determined by means of the equation applicable for this purpose (taken from Ullmanns Encykl. d. Techn. Chem., Vol. 22, Verlag Chemie Weinheim, 4th edition, page 294 (1982))

$$\lg p(T) = 7.0916 - \frac{1457.3}{211.24 + T}$$

where $p(T)$ is the pressure in hPa at $T$ ° C. and lg is the logarithm to the base 10. The procedure for determining a suitable component ($b_1$) is then similar to that described above.

For other vinyl-containing compounds, the vapor pressure data are often also available in the analytical form of an appropriate equation or can be easily determined.

If, for example, a mixture of vinyl-containing compounds, such as a mixture of styrene and divinylbenzene, is to be stabilized in the vapor phase—the boiling points here are 145.8° C. and 195° C., respectively, at atmospheric pressure (the latter for a mixture of the m- and p-isomers in the ratio of 75:25)—the pressure/temperature data of the lower-boiling (lowest-boiling) compound, in this case styrene, serve as a basis for selecting the readily volatile nitroxyl compound as component ($b_1$) and the corresponding data of the isomer mixture of the divinylbenzene, as the higher-boiling compound, serve as a basis for selecting the sparingly volatile nitroxyl compound as component ($b_2$). If a plurality of readily volatile nitroxyl compounds are to be used, that having the lowest vapor pressure (ie. the highest-boiling nitroxyl compound) must likewise fulfill the criterion according to the invention at the reference temperature.

If compounds which have excessively high volatilities are used as component ($b_1$), it is to be feared that (some of) these nitroxyl compounds will pass over into the distillate where they may interfere with further reactions (eg. polymerizations) of the purified vinyl-containing compounds.

Without carrying out further detailed estimations or calculations as above, a comparison of Tables 2 and 3 with Table 1 immediately reveals that it should be possible to use all nitroxyl compounds of Table 1 or mixtures of these compounds as component ($b_1$) for stabilizing virtually all vinyl-containing compounds of Tables 2 and 3 or mixtures thereof.

In the case of vinyl methyl ether, which has a boiling point of 5.5° C. at atmospheric pressure, the vapor pressure of the compound Tempol may be too low at this temperature, ie. the value might be below the lower percentage limit of the selection criterion. An estimate as carried out by way of example above gives for this nitroxyl compound vapor pressures of from 0.083 to 0.17 hPa at 5.5° C. and hence of from 0.0082 to 0.017% based on the vapor pressure of vinyl methyl ether (1013 hPa). The proportion of this nitroxyl compound may therefore be too low for stabilizing the vinyl methyl ether in the vapor phase. A decision would have to be made here on the basis of more extensive data and experiments, but of course the tendency to free radical polymerization is substantially reduced in this temperature range.

Since the vapor pressure curves of the vinyl-containing compounds and of the volatile nitroxyl compounds suitable for their vapor phase stabilization are as a rule parallel or virtually parallel at least over wide pressure/temperature ranges, the potential suitability of a nitroxyl compound, found for one or more pressure/temperature pairs, should also be valid for other pressure/temperature conditions.

If it is intended to add aromatic nitro compounds and/or iron compounds as components ($b_3$) and ($b_4$) and, if required, further costabilizers, the compounds usually used here are those which have little or no volatility under the pressure/temperature conditions considered. However, it may be entirely desirable here too, as in the case of the nitroxyl compounds of components ($b_1$) and ($b_2$), to use combinations of appropriate readily volatile and sparingly volatile compounds. The selection criteria for this purpose are then preferably to be applied completely analogously to the criteria for selecting the nitroxyl compounds of components ($b_1$) and ($b_2$).

It should also be noted here that the actual gas-phase partial pressures of components ($b_1$), where relevant ($b_3$) and/or where relevant ($b_4$), and of any costabilizers present may, owing to intermolecular interactions in the gas and liquid phase, easily differ from the values to be expected from the Henry-Dalton law and hence from the composition of the liquid phase. Since furthermore the vapors of the components in the gas phase do not as a rule behave as ideal gases, it is frequently possible in calculations to make only general estimates of the ratios of the components relative to one another in the vapor space. However, it is generally possible here easily and rapidly to obtain information about the respective compositions by analysis of the vapor phase (of the condensed vapor) and of the liquid phase and to correlate this information with the stabilization effects.

Furthermore, as a result of reactions of the components with one another or with the vinyl-containing compounds, derivatives which are more readily volatile may form or readily volatile compounds may be converted into compounds which are more sparingly volatile. All that is noted here is the readiness of various iron compounds (as possible component ($b_4$)) to form π-complexes with vinyl-containing compounds or aromatic nitro compounds.

We claim:

1. A mixture comprising (A) at least one vinyl-containing compound, (B) a stabilizer comprising ($b_1$) a nitroxyl compound of a secondary amine having no hydrogen atoms on the α carbon atoms, whose vapor pressure at the boiling point of the lowest-boiling vinyl-containing compound from (A) is from 0.01 to 50% of the vapor pressure of the lowest-boiling vinyl-containing compound (A), or a mixture of nitoxyl compounds of secondary amines having no hydrogen atoms on the α carbon atoms, in which the vapor pressure of the highest-boiling nitroxyl compound at the boiling point of the lowest-boiling vinyl-containing compound from (A) is from 0.01 to 50% of the vapor pressure of the lowest-boiling vinyl-containing compound from (A), ($b_2$) a nitroxyl compound of a secondary amine having no hydrogen atoms on the α carbon atoms, whose vapor pressure at the boiling point of the highest-boiling vinyl-containing compound from (A) is less than 0.01% of the vapor pressure of the highest-boiling vinyl-containing compound from (A), or a mixture of nitroxyl compounds of secondary amines having no hydrogen atoms on the α carbon atoms, in which the vapor pressure of the lowest-boiling nitroxyl compound at the boiling point of the highest-boiling vinyl-containing compound from (A) is less than 0.01% of the vapor pressure of the highest-boiling vinyl-containing compound from (A), wherein ($b_1$) and ($b_2$) the vapor pressure of the nitroxyl compound and the vapor pressure of a vinyl-containing compound at the boiling point of the vinyl containing compound is taken as the reference, and optionally ($b_3$) at least one aromatic nitro compounds and/or ($b_4$) at least one iron compounds.

2. The mixture as claimed in claim 1, wherein component (A) comprises, a vinyl-containing compound of formula Ia

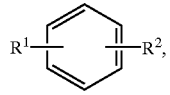

Ia where

R$^1$ is hydrogen, $C_1$–$C_4$-alkyl, $C_2$–$C_4$-alkenyl, carboxyl, formyl, sulfo, hydroxyl, amino or nitro, and R$^2$ is $C_2$–$C_4$-alkenyl and/or a vinyl-containing compound of formula Ib

Ib where

R$^3$ is hydrogen or $C_1$–$C_4$-alkyl, and

R$^4$ is $C_2$–$C_4$-alkenyl.

3. The mixture as claimed in claim 2, wherein component ($b_1$) comprises at least one compound of formula IIIa

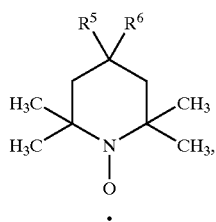

where
R⁵ is hydrogen, and
R⁶ is hydrogen, hydroxyl, $C_1$–$C_4$-alkoxy, $C_1$–$C_6$-acyloxy or tri($C_1$–$C_4$-alkyl)-silyloxy, or $CR^5R^6$ together are carbonyl, and
component ($b_2$) comprises at least one compound of formula IIIb

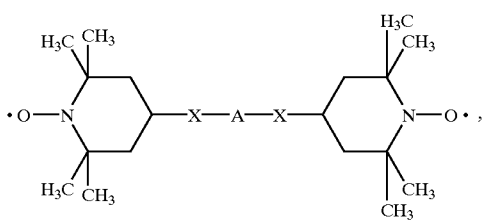

where
X is oxygen or $R^1$—N,
A is $C_6$–$C_{12}$-alkylene, α,ω-bis(carbonyloxy)-$C_6$–$C_{12}$-alkylene, α,ω-$C_6$–$C_{12}$-diacyl, 1,2-, 1,3- or 1,4-phenylene, phthaloyl, isophthaloyl or terephthaloyl, and
$R^7$ is hydrogen, $C_1$–$C_4$-alkyl or $C_1$–$C_6$-acyl.

4. The mixture as claimed in claim 1, wherein component (A) comprises, a vinyl-containing compound of formula II $$CH_2=CZ^4-Q-Z^1 \qquad (II)$$

where
Q is a single chemical bond, oxygen or —$NZ^2$—,
$Z^1$ is

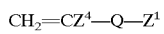

or —$Z^3$,
$Z^2$, $Z^4$ are each hydrogen or $C_1$–$C_4$-alkyl and
$Z^3$ is hydrogen, hydroxyl, cyano, $C_1$–$C_8$-alkoxy, $C_1$–$C_8$-alkyl or a radical which, together with $Z^2$ or $Z^4$, forms a saturated or unsaturated $C_3$-, $C_4$-, $C_5$- or $C_6$-alkylene bridge in which up to two non-neighboring carbon atoms may be replaced by N, NH, N($C_1$–$C_4$-alkyl), N($C_6$–$C_{10}$-aryl) or oxygen.

5. The mixture as claimed in claim 1, wherein the stabilizer (B) comprises at least one compound of formula IIIa as component ($b_1$) and at least one compound of formula IIIb as component ($b_2$)

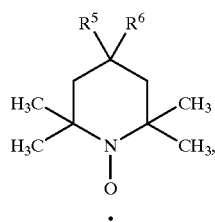

where
R⁵ is hydrogen, and
R⁶ is hydrogen, hydroxyl, $C_1$–$C_4$-alkoxy, $C_1$–$C_6$-acyloxy or tri($C_1$–$C_4$-alkyl)-silyloxy, or $CR^5R^6$ together are carbonyl, and

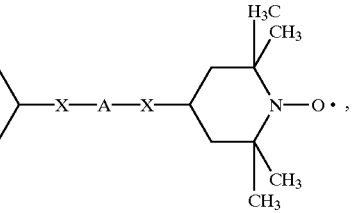

where
X is oxygen or $R^7$—N,
A is $C_6$–$C_{12}$-alkylene, α,ω-bis(carbonyloxy)-$C_6$–$C_{12}$-alkylene, α,ω-$C_6$–$C_{12}$-diacyl, 1,2-, 1,3- or 1,4-phenylene, phthaloyl, isophthaloyl or terephthaloyl, and
$R^7$ is hydrogen, $C_1$–$C_4$-alkyl or $C_1$–$C_6$-acyl.

6. The mixture as claimed in claim 5, wherein the stabilizer (B) comprises at least one aromatic nitro compound as additional component ($b_3$).

7. The mixture as claimed in claim 5, wherein the stabilizer (B) comprises at least one iron compound as additional component ($b_4$).

8. The mixture as claimed in claim 5, wherein the stabilizer (B) comprises at least one aromatic nitro compound as additional component ($b_3$) and at least one iron compound as additional component ($b_4$).

9. The mixture as claimed in claim 1, wherein at least one aromatic nitro compound ($b_3$) is present.

10. The mixture as claimed in claim 1, wherein at least one iron compound ($b_4$) is present.

11. A process for inhibiting the premature polymerization of vinyl-containing compounds, said process comprising
adding a stabilizer (B) in an effective amount to said vinyl-containing compounds before or during a purification or distillation
wherein stabilizer (B) comprises
($b_1$) a nitroxyl compound of a secondary amine having no hydrogen atoms on the α carbon atoms, whose vapor pressure at the boiling point of the lowest-boding vinyl-containing compound torn (A) is from 0.01 to 50% of the vapor pressure of the lowest boiling vinyl-containing compound (A), or
a mixture of nitroxyl compounds of secondary amines having no hydrogen atoms on the α carbon atoms, in which the vapor pressure of the highest-boiling nitoxyl compound at the boiling point of the lowest-boiling vinyl-containing compound from (A) is from 0.01 to 50% of the vapor pressure of the lowest-boiling vinyl-containing compound from (A), (b$_2$) a nitroxyl compound of a secondary amine having no hydrogen atoms on the α carbon atoms, whose vapor pressure at the boiling point of the highest-boiling vinyl-containing compound from (A) is less than 0.01% of the vapor pressure of the highest-boiling vinyl-containing compound from (A), or a mixture of nitroxyl compounds of secondary amines having no hydrogen atoms on the α carbon atoms, in which the vapor pressure of the lowest-boiling nitroxyl compound at the boiling point of the highest-boiling vinyl-containing compound from (A) is less than 0.01% of the vapor pressure of the highest-boiling vinyl-containing compound from (A), wherein (b$_1$) and (b$_2$) the vapor pressure of the nitroxyl compound and the vapor pressure of a vinyl-containing compound at the boiling point of the vinyl containing compound is taken as the reference, and optionally (b$_3$) at least one aromatic nitro compounds and/or (b$_4$) at least one iron compounds.

12. A process for inhibiting the premature polymerization of vinyl-containing compounds, said process comprising adding a stabilizer (B) individually or in at least two groups to said vinyl-containing compounds before or during a purification or distillation, wherein stabilizer (B) comprises (b$_1$) a nitroxyl compound of a secondary amine having no hydrogen atoms on the α carbon atoms, whose vapor pressure at the boiling point of the lowest-boiling vinyl-containing compound from (A) is from 0.01 to 50% of the vapor pressure of the lowest-boiling vinyl-containing compound (A), or a mixture of nitroxyl compounds of secondary having no hydrogen atoms on the α carbon atoms, in which the vapor pressure of the highest-boiling nitroxyl compound at the boiling point of the lowest-boiling vinyl-containing compound from (A) is from 0.01 to 50% of the vapor pressure of the lowest-boiling vinyl-containing compound from (A), (b$_2$) a nitroxyl compound of a secondary amine having no hydrogen atoms on the α carbon atoms, whose vapor pressure at the boiling point of the highest-boiling vinyl-containing compound from (A) is less than 0.01% of the vapor pressure of the highest-boiling vinyl-containing compound from (A), or a mixture of nitroxyl compounds of secondary amines having no hydrogen atoms on the α carbon atoms, in which the vapor pressure of the lowest-boiling nitroxyl compound at the boiling point of the highest-boiling vinyl-containing compound from (A) is less than 0.01% of the vapor pressure of the highest-boiling vinyl-containing compound from (A), wherein (b$_1$) and (b$_2$) the vapor pressure of the nitroxyl compound and the vapor pressure of a vinyl-containing compound at the boiling point of the vinyl containing compound is taken as the reference, and optionally (b$_3$) at least one aromatic nitro compounds and/or (b$_4$) at least one iron compounds.

* * * * *